United States Patent
Sobotta (10) Patent No.: US 9,486,644 B2
(45) Date of Patent: Nov. 8, 2016

(54) METHOD AND SYSTEM FOR DOSE DETERMINATION OF RADIATION THERAPY

(71) Applicant: Benjamin Sobotta, Ulm (DE)

(72) Inventor: Benjamin Sobotta, Ulm (DE)

(73) Assignee: Benjamin Sobotta, Ulm (DE)

( * ) Notice: Subject to any disclaimer, the term of this patent is extended or adjusted under 35 U.S.C. 154(b) by 208 days.

(21) Appl. No.: 14/144,615

(22) Filed: Dec. 31, 2013

(65) Prior Publication Data

US 2014/0275703 A1 Sep. 18, 2014

Related U.S. Application Data

(60) Provisional application No. 61/790,670, filed on Mar. 15, 2013.

(51) Int. Cl.
*A61N 5/10* (2006.01)

(52) U.S. Cl.
CPC ................... *A61N 5/1031* (2013.01)

(58) Field of Classification Search
CPC .. A61N 5/1031; A61N 5/103; A61N 5/1042; A61N 2005/1034; A61N 5/1045; A61N 5/00; A61N 5/10; A61N 5/1039; A61N 5/1077
See application file for complete search history.

(56) References Cited

U.S. PATENT DOCUMENTS

| | | | | |
|---|---|---|---|---|
| 6,735,277 | B2 * | 5/2004 | McNutt | A61N 5/1031 378/64 |
| 7,688,938 | B2 * | 3/2010 | Paliwal | A61B 6/032 378/16 |
| 2003/0212325 | A1 * | 11/2003 | Cotrutz | A61N 5/1031 600/436 |
| 2013/0102830 | A1 * | 4/2013 | Otto | A61N 5/1031 600/1 |

* cited by examiner

*Primary Examiner* — Christine H Matthews
*Assistant Examiner* — Joshua D Lannu (57) ABSTRACT

Methods for performing dose determination and cost function gradients in a radiation therapy are disclosed, which include: discretizing a volume-of-interest (VOI) into a set of voxels; identifying a set of beamlets which deposit dose contributions of radiation to the VOI, and each beamlet has a weight factor; transforming the dose contributions into a first domain, and transforming the weight factors into a second domain orthogonal to the first domain; calculate the local derivatives of a cost function of dose and cost function gradients with respect to the weights of the beamlets.

12 Claims, 8 Drawing Sheets

METHOD AND SYSTEM FOR DOSE DETERMINATION OF RADIATION THERAPY

RELATED APPLICATION

This is a non-provisional application based upon U.S. provisional patent application Ser. No. 61/790,670, filed Mar. 15, 2013, which is incorporated herein by reference.

TECHNICAL FIELD

The disclosure relates planning and delivery of radiation in radiation therapy. In particular, methods and systems are provided for determining dose distributions in a radiation therapy.

BACKGROUND

Radiation therapy involves the transmission of radiation energy to a tumor site (or volume-of-interest) within the patient to control cell growth. Radiation therapy may be curative in a number of types of cancer if they are localized to one area of the body.

Radiation therapy treatment planning may be carried out according to a forward planning technique or an inverse planning technique. Forward planning involves delivering an initial planned radiation dose and then delivering subsequent doses by observation or inference of the efficacy of the preceding dose in a trial-and-error manner. The determination of dose delivery by forward planning is therefore performed according to human observation and experience. Inverse planning instead seeks to calculate an optimized dose delivery and then work backwards to determine the appropriate radiation beam characteristics to deliver that optimized dose. Inverse planning of radiation therapy for tumors may be performed for Tomotherapy, or other Intensity Modulated Radiation Therapy (IMRT) radiation delivery techniques employing ionizing photon radiation or any other ionizing radiation like e.g. protons, heavy ions, or electrons. These techniques involve transmission of radiation beams, usually collimated by an appropriate collimation device like a multi-leaf collimator (MLC), toward the volume-of-interest (VOI) from various angular orientations.

Radiation dose can damage or kill both cancerous and healthy tissue cells. A radiation beam originating from a radiation source and projection through a subject will deposit radiation dose along its path. It is typical that some healthy tissue will receive radiation dose during a radiation treatment. In order to ensure that the patient is optimally treated, it is necessary to predict and shape a dose distribution in treatment planning of radiation therapy. Dose is deposited energy by some treatment devices applying ionizing radiation to a patient or measurement device (or in other words, VOI), and being computed in a point or a number of points. The dose at any given position inside a VOI is composed of a weighted superposition of elementary doses. Elementary dose is dose deposited during a certain time interval and/or a certain configuration of the treatment device.

Two quantities are of interest in treatment planning and form the basis of all planning algorithms:
1. The dose to any point in a VOI;
2. The derivative of a cost function of dose at any point with respect to its elementary constituents.

Current techniques for evaluating these two quantities are cumbersome and time-consuming. There is a desire for improvement of systems and methods for determining the above two quantities quickly and accurately, which is important not only for designing good radiation treatment plans, but also for the successful implementation of further interactive adaptive treatment techniques.

BRIEF SUMMARY

According to an aspect of the present disclosure, a method for performing dose determination in a radiation therapy, including: creating a set of voxels from a volume of interest in a physical object or system, or virtual model thereof; identifying a plurality of beamlets, each of said beamlets depositing a dose contribution of radiation to at least one subset of said voxels; transforming the dose contributions of all beamlets for each of said voxels into a first domain, yielding a set of transformed dose contributions for each of said voxels; assigning a weight to each of said beamlets to create a set of weights; transforming the set of weights into a second domain orthogonal to the first domain, yielding a set of transformed weights; and determining a dose for each of said voxels through summing up the elementwise product of the set of transformed dose contributions and the set of transformed weights. The first domain and second domain are the same, and the first domain is a sparse domain.

According to a further aspect of the present disclosure, the method further includes setting non-significant elements of the set of transformed dose contributions to zero. The non-significant elements may be identified by a threshold.

According to a further aspect of the present disclosure, the method further includes dropping non-significant elements that are defined for each of said voxels.

According to another aspect of the present disclosure, a method for determining a gradient of a cost function of dose is disclosed, having: creating a set of voxels from a volume of interest in a physical object or system, or virtual model thereof; identifying a plurality of beamlets, each of said beamlets depositing a dose contribution of radiation to at least one subset of said voxels; transforming the dose contributions of all beamlets for each of said voxels into a first domain, yielding a set of transformed dose contributions from each of said beamlets; associating a weight with each of said beamlets; identifying a dose for each of said voxels; identifying a cost function of said dose; computing the gradient of the cost function with respect to the dose in each voxel; and determining the transform of the gradient of the cost function with respect to each of said weights in the first domain through summing up the elementwise products of the set of transformed dose contributions and the cost function gradient with respect to the dose in each voxel. Having determined said quantity, applying a transform from the first domain yielding the gradient of the cost function with respect to each of said weights.

According to a further aspect of the present disclosure, the method further includes setting non-significant elements of the set of transformed dose contributions to zero. Said non-significant elements may be identified by a threshold.

According to a further aspect of the present disclosure, the method further includes dropping non-significant elements that are defined for each of said voxels.

According to another aspect of the present disclosure, a non-transitory computer readable medium is disclosed, having stored thereon instructions that when executed cause one or more processors to perform the steps of: creating a set of voxels from a volume of interest in a physical object or system; identifying a plurality of beamlets, each of said beamlets depositing a dose contribution of radiation to at least one subset of said voxels; transforming the dose contributions of all beamlets for each of said voxels into a first domain, yielding a set of transformed dose contributions for each of said voxels; assigning a weight to each of said beamlets to create a set of weights; transforming the set of weights into a second domain orthogonal to the first domain, yielding a set of transformed weights; and determining a dose for each of said voxels through summing up the elementwise product of the set of transformed dose contributions and the set of transformed weights.

According to another aspect of the present disclosure, a non-transitory computer readable medium is disclosed, having stored thereon instructions that when executed cause one or more processors to perform the steps of: creating a set of voxels from a volume of interest in a physical object or system, or virtual model thereof; identifying a plurality of beamlets, each of said beamlets depositing a dose contribution of radiation to at least one subset of said voxels; transforming the dose contributions of all beamlets for each of said voxels into a first domain, yielding a set of transformed dose contributions from each of said beamlets; associating a weight with each of said beamlets; identifying a dose for each of said voxels; identifying a cost function of said dose; computing the gradient of the cost function with respect to the dose in each voxel; and determining the transform of the gradient of the cost function with respect to each of said weights in the first domain through summing up the elementwise products of the set of transformed dose contributions and the cost function gradient with respect to the dose in each voxel. Having determined said quantity, applying a transform from the first domain yielding the gradient of the cost function with respect to each of said weights.

DETAILED DESCRIPTION

The disclosed embodiments relate to methods and systems for dose determination to tumor sites (or VOI) in a patient in radiation therapy. During radiation dose delivery, radiation scattering commonly occurs due to the passage of the radiation through the body volume. These scatter effects are taken into account during the computation of the distribution of dose deposited by the radiation. Dose in a point or a plurality of points in a VOI is computed by a superposition of a plurality of elementary doses, each with its individual weight factor:

$$D = t \cdot \phi, \qquad (1)$$

where D denotes a dose in a point of VOI, t is a vector of elementary doses, and $\phi$ is a vector of the respective weight factors.

Figure 1:
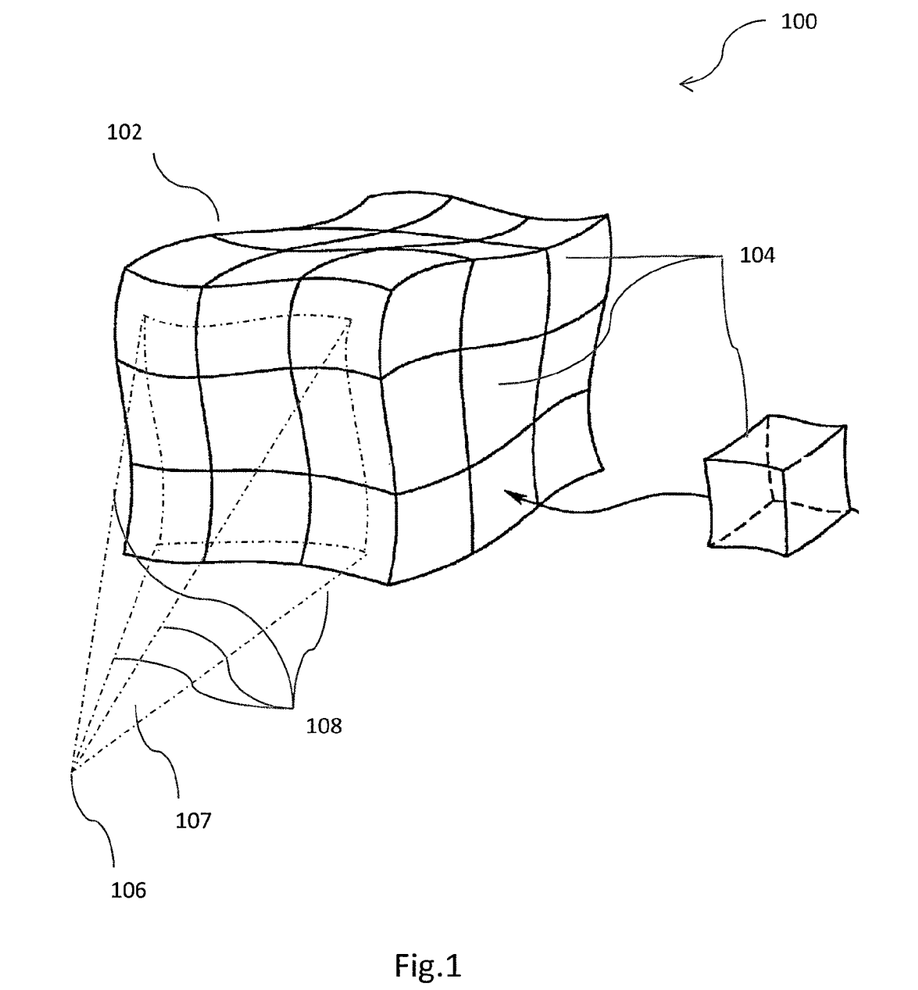
FIG. 1 is an illustrative example of the grid system which is compiled from a $3^3$ arrangement of voxels having bent rectangular regions.

Referring now to FIG. 1, VOI 102 is irradiated by a radiation beam 107 originating from a radiation source 106. For the reason of simplicity, current embodiment only discloses one radiation beam irradiating a VOI. It is to be understood that, however, in some other embodiments, more than one radiation beam may be projected on a VOI. VOI 102 can be organs, tissues, or any body parts of a patient that need to be irradiated. However, it is understood that VOI 102 can also be any experimental object that is used such as for researching or testing purposes.

Typically, VOI 102 has an irregular shape. It is broken down into a plurality of subvolumes, so-called voxels 104 as illustrated in FIG. 1. Voxels 104 may be regular or irregular in shape, as depicted. VOI 102, or in other words, the plurality of voxels 104, are projected by a single beam 107.

The single beam 107 can be divided into a multiple of elementary beams, so-called beamlets 108. Each of these beamlets 108 is configured to deliver a dose to a respective subset of voxels 104, which may include one or more voxels 104. However, due to the scatter effects, any beamlet 108 may not only deliver a dose to the subset of voxels it is directly impinging on, but also deposit a dose within other voxels within the VOI 102 (in fact, other body volume of a patient besides the VOI, may also get irradiated by any beamlet 108). In other words, each of these beamlets 108 may deposit a dose, so called elementary dose, to each voxel 104. Consequently, the dose in a voxel 104 consists of each elementary dose deposited on the voxel 104 by all beamlets 108.

Assuming the number of voxels in a VOI is $N_v$, the number of beamlets in a beam is $N_b$, and further assuming that each beamlet is assigned with a weight factor, e.g. a beamlet j is assigned a weight factor $\phi_j$, the dose in a voxel i is then expressed as a linear combination of weighted dose contribution of each beamlet as follows:

$$D_i = \sum_j T_{ij} \varphi_j, \quad j = 1, \ldots, N_b, \qquad (2)$$

where $D_i$ denotes the dose deposited in voxel i from a beam. $T_{ij}$ denotes the dose contribution of beamlet j to voxel i, or in other words, $T_{ij}$ denotes the dose contribution received by voxel i deposited from beamlet j. The dose contribution of each beamlet j, where j=1, ..., $N_b$, to each voxel i, where i=1, ..., $N_v$, forms a set of dose contributions, or more precisely, forms a $N_v \times N_b$ matrix $T_{ij}$. $\phi_j$ is the weight factor of beamlet j. In some embodiments, each beamlet inside a beam can be assigned with equal weight. In some embodiments, each beamlet inside a beam can be assigned with various weight values. In other embodiments, each beamlet inside a beam can also be assigned with non-constant weights. The weight factor of each beamlet j, where j=1, ..., $N_b$, forms a set of weight factors, or more precisely, forms a vector $\Phi$ with a length of $N_b$.

For dose determination in a radiation therapy, not only the dose to each voxel $D_i$, but also the derivative of a function of dose at any voxel with respect to its elementary constituents is required. This function is also sometimes termed as a "cost function" or an "objective function". The elementary constituents can be e.g. the weight factors of beamlets. The derivative of a cost function with respect to each weight factor is computed for optimization. The latter yields an optimal weight factor of each beamlet.

By the virtue of chain rule, the gradient of a cost function $f(D)$ of dose D with respect to a weight factor $\phi_j$ can be expressed as:

$$\frac{\partial f(D)}{\partial \varphi_j} = \sum_i \frac{\partial f(D)}{\partial D_i} \cdot \frac{\partial D_i}{\partial \varphi_j}, \quad i = 1, \ldots, N_v \quad (3)$$

where D denotes the dose in a VOI consisting of a plurality of voxels, $D_i$ denotes the dose deposited in voxel i, $f(D)$ is a cost function, and $\phi_j$ denotes the weight factor of beamlet j. From equation (2), equation (3) can be further expressed as:

$$\frac{\partial f(D)}{\partial \varphi_j} = \sum_i \frac{\partial f(D)}{\partial D_i} \cdot T_{ij}, \quad i = 1, \ldots, N_v, \quad (4)$$

where $T_{ij}$ denotes the dose contribution of beamlet j to voxel i.

However, in operation, it is typical that a VOI is divided into an enormous number of voxels, and a beam is also split into a vast number of beamlets. In other words, both $N_v$ and $N_b$ can be numbers having very large order of magnitude. This leads to computation of formulae (2) and (4) for all the voxels inside a VOI and all beamlets becoming very time-consuming due to large numbers of arithmetic operations. Therefore, improved methods for accelerating of computing the dose and the derivative of a cost function are required.

One approach is performing a transformation of the set of dose contributions and the set of weight factors into orthogonal domains.

Said transformation of the set of dose contributions is denoted as Z and the transformation of the set of weight factors is denoted as Y. They need to fullfill one basic requirement:
the scalar product remains unchanged, i.e. Z and Y are orthogonal:

$$t \cdot \phi = Z(t) \cdot Y(\phi)$$

To achieve said acceleration, the domain Z transforms into is sparse, i.e. the information present in vector t is statistically concentrated in only a few coefficients of the transformed vector $Z(t)$.

Equation (1) for calculating the dose in a point can be expressed as:

$$D = Z(t) \cdot Y(\phi)$$

By applying the Z-transform to all $N_v$ row vectors t in matrix T, i.e. equation (2) for calculating the dose in voxel i, can be expressed as $$D_i = Z(T)_{ij} \cdot Y(\phi)_j$$

Non-significant elements can be identified and dropped, in effect, rendering the matrix Z(T) sparse. The i-th row of Z(T) now contains $k_i$ significant elements, where $k_i$ is a much smaller number compared to $N_b$. This may lead to a significant reduction of the arithmetic operations of dose calculation, since $k_i \ll N_b$. In some embodiments, a single method can be applied to identify non-significant elements. In other embodiments, the method may vary across Z(T).

Further, since the majority of members of Z(T) are 0, only the non-zero members of Z(T) are saved in a storage, which leads to a reduction of the storage space. Choosing the relative amount of zero-entries of Z(T) allows to adjust the trade-off between computation speed and accuracy. Or more precisely, dropping less elements of Z(T) keeps the dose $D = Z(T)Y(\phi)$ more accurate.

A further approach is performing a transformation of the set of dose contributions to compute the derivative of a cost function of dose with respect to the weights of its constituents.

Said transformation of the set of dose contributions is denoted as Z. It needs to fullfill one basic requirement, namely that there exists an transform U such that $$x = U(Z(x))$$

for any given $N_v$-element vector x.

Then equation (4) for calculation the derivative of a cost function with respect to a weight factor $\phi$ can then be expressed as:

$$\frac{\partial f(D)}{\partial \varphi_j} = \frac{\partial f(D)}{\partial D_i} T_{ij} = U\left(\frac{\partial f(D)}{\partial D_i} Z(T_{ij})\right)$$

Non-significant elements can be identified and dropped, in effect, rendering the matrix $Z(T)_{ij}$ sparse. The i-th row of Z(T) now contains $k_i$ significant elements, where $k_i$ is a much smaller number compared to $N_b$. This may lead to a significant reduction of the arithmetic operations of the cost function gradient calculation, since $k_i \ll N_b$. In some embodiments, a single method can be applied to identify non-significant elements. In other embodiments, the method may vary across Z(T).

Further, since the majority members of Z(T) are 0, only the non-zero members of Z(T) are saved in a storage, which leads to a reduction of the storage space. Choosing the relative amount of zero-entries of Z(T) allows to adjust the trade-off between computation speed and accuracy. Or more precisely, dropping less elements of Z(T) keeps the derivative of f(D) with respect to the weight factors $\phi_j$ more accurate.

Figure 2:
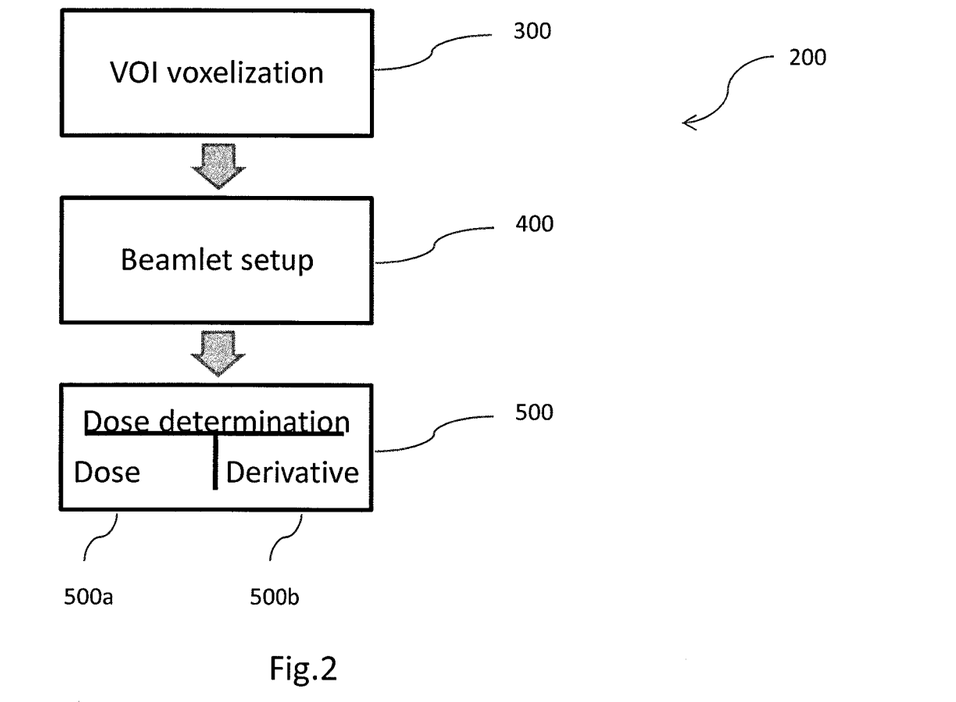
FIG. 2 is a flowchart of an overall process used in dose determination according to described embodiments.

Turning now to the drawings, FIG. 2 is a block diagram illustrating a process 200 for dose determination in a radiation therapy according to embodiments of the disclosure. Process 200 executes a number of sequential steps which include VOI discretization 300, beam and beamlet setup 400, and dose determination 500, wherein dose determination 500 includes dose calculation 500a and cost function derivative calculation 500b. These subprocesses are described in further detail below, with reference to FIGS. 3 to 5.

Figure 3:
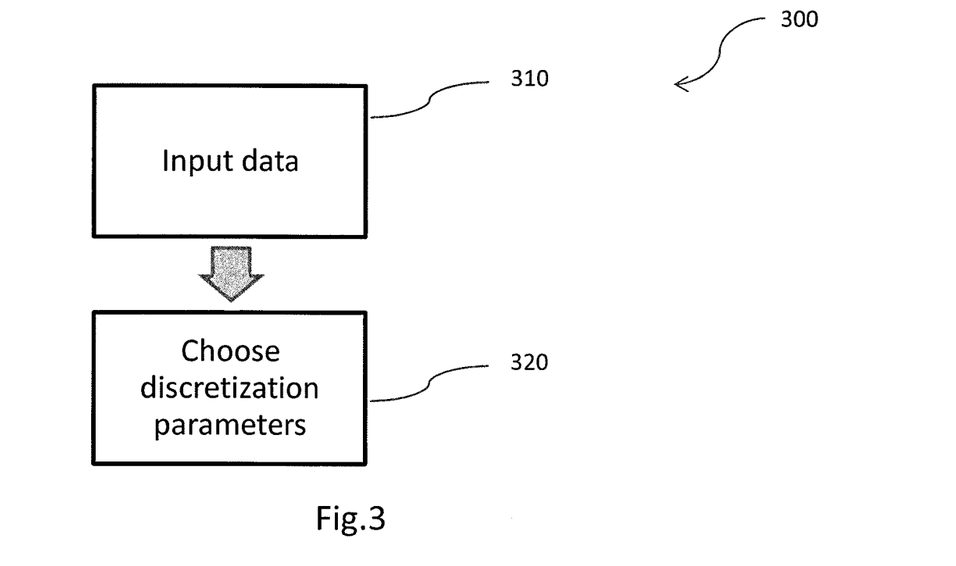
FIG. 3 is a flowchart of a VOI discretization subprocess of the process shown in FIG. 2.

Referring now to FIG. 3, VOI discretization subprocess 300 is described in further detail. In some embodiments, a VOI can be a tumor site in a patient. In other embodiments, a VOI can also be an object detected in a measurement device. VOI discretization subprocess 300 executes two sequential steps which include inputting data 310 and choosing discretization parameters 320.

The VOI discretization subprocess 300 handles input data from e.g. CT scans, as shown in step 310. Once the input data is received at step 310, the discretization parameters (may include e.g. voxel size or resolution) to be used for radiation therapy, or more precisely for radiation dose determination, can be chosen. This information is then used to generate a discretized representation of the input data. After the VOI has been discretized, subprocess 300 feeds into beam and beamlet setup subprocess 400.

Figure 4:
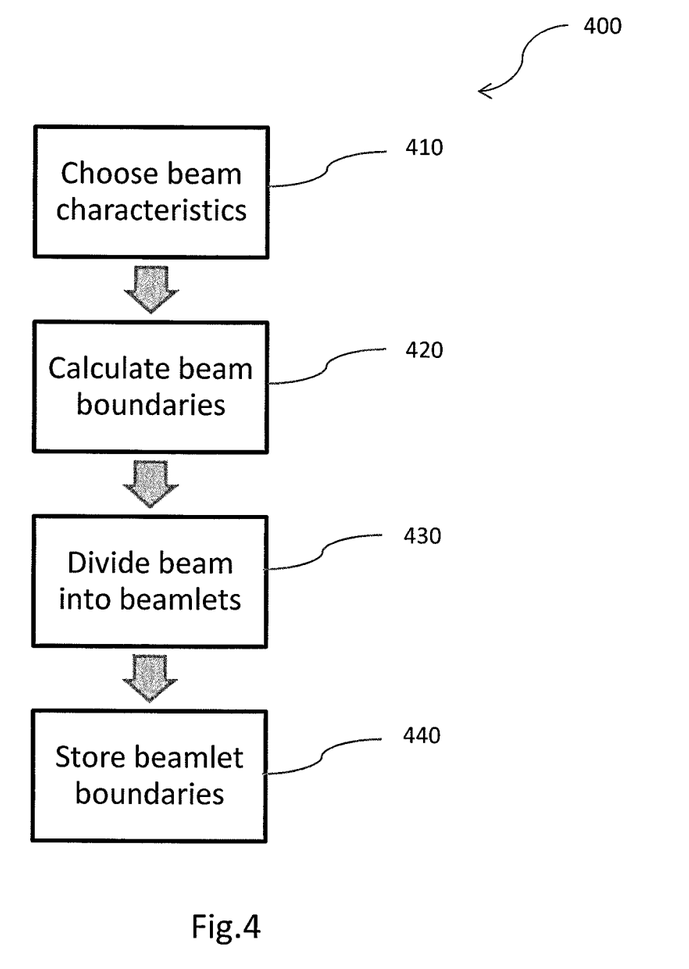
FIG. 4 is a flowchart of a beam and beamlet setup subprocess of the process shown in FIG. 2.

Referring now to FIG. 4, beam and beamlet setup subprocess 400 is described. Beam and beamlet setup subprocess 400 determines the boundaries of each beam and divides the beams into beamlets, calculates the beamlet boundaries and determines which voxels receive a dose contribution from each beamlet.

Subprocess 400 begins with data input from the user (i.e. medical personnel planning the dose delivery) as to the desired radiation beam characteristics, at step 410. At this step, the user also inputs beam setup information, such as the distance between the radiation source and the VOI isocenter.

Figure 7:
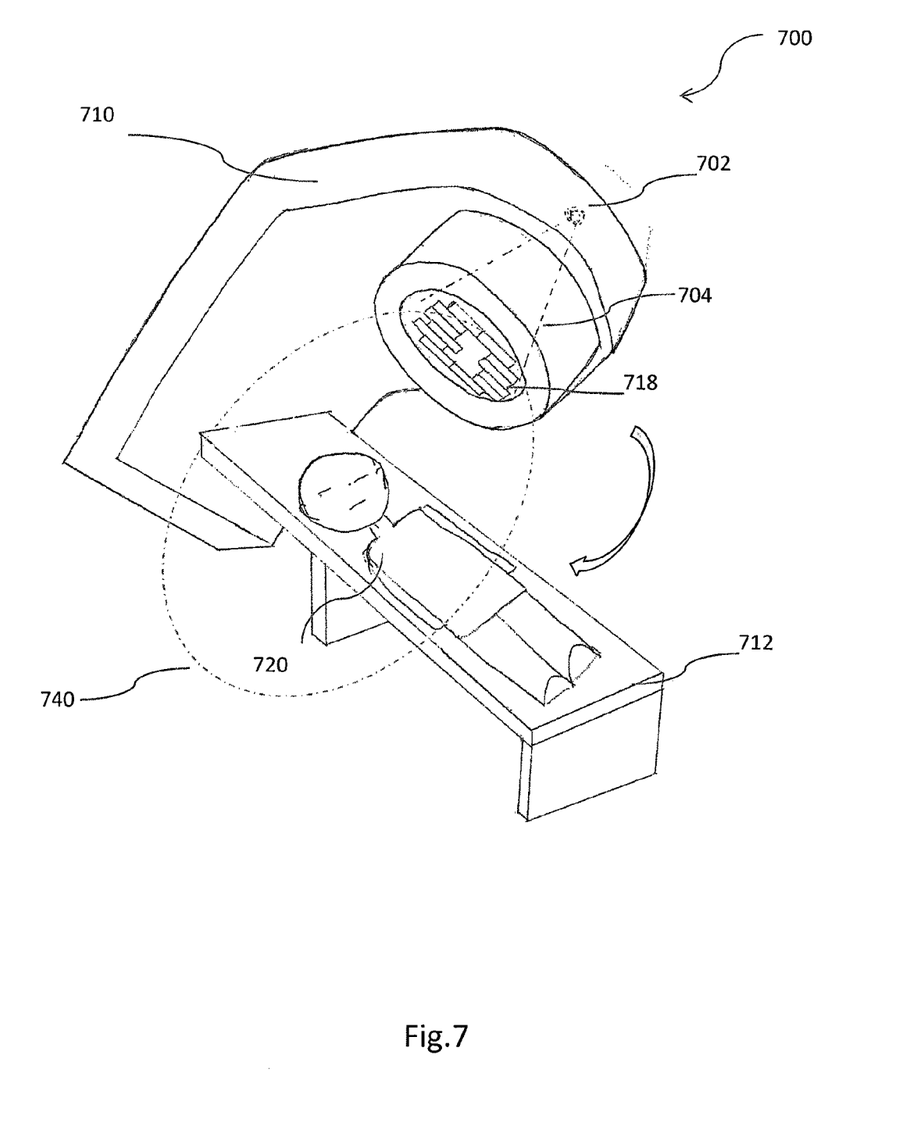
FIG. 7 is a schematically depicts an example radiation delivery apparatus that may be used in a radiation therapy.

For radiation therapy, the radiation beams are typically delivered to a patient lying on a bed while a gantry carrying a radiation beam emitter moves around the patient as depicted in FIG. 7. A radiation therapy apparatus 700 may include gantry 710 and bed 712. Radiation beam 704 emitted from radiation source 702 toward subject 720 is permitted to pass through multi-leaf collimator 718 for beam shaping. The gantry 710 can be positioned at numerous different angles around trace 740, depending on the dose delivery plan developed by the radiation oncologist and the limitations of the radiation delivery apparatus.

Turing back to FIG. 4 now, after the beam characteristics are chosen at step 410, the beam boundaries are then calculated at step 420. At a given gantry angle, the position and width of the beam is calculated in order to fully cover the VOI as seen by the beam source from the radiation beam emitter. In the current embodiment, merely one beam is irradiated from a radiation beam emitter to a VOI, however, it is understandable that multiple beams may be emitted in a radiation therapy.

Once the planned beam boundaries are determined at step 420, the beam is divided into beamlets at step 430. The number of beamlets within each beam can depend on the tumor-shape, gantry angle, equipment limitations, beam boundaries and so on.

At step 440, for a given gantry angle, the respective beam, beamlets, and the voxels within the VOI through which each beam and beamlet contribute dose to, are stored. Then the gantry can move to the next predetermined angles, and sub-steps 420 to 440 are repeated till beam and beamlets are stored for all predetermined gantry angles.

After the last gantry angle has been processed at step 440, subprocess 400 feeds into dose determination subprocess 500.

During the dose determination subprocess 500, two aspects of information are determined: dose to each voxel in a VOI, and the derivative of a cost function with respect to each beamlet weight factor. The former is determined through subprocess 500a in FIG. 5A, and the latter is determined through subprocess 500b in FIG. 5B.

Figure 5A:
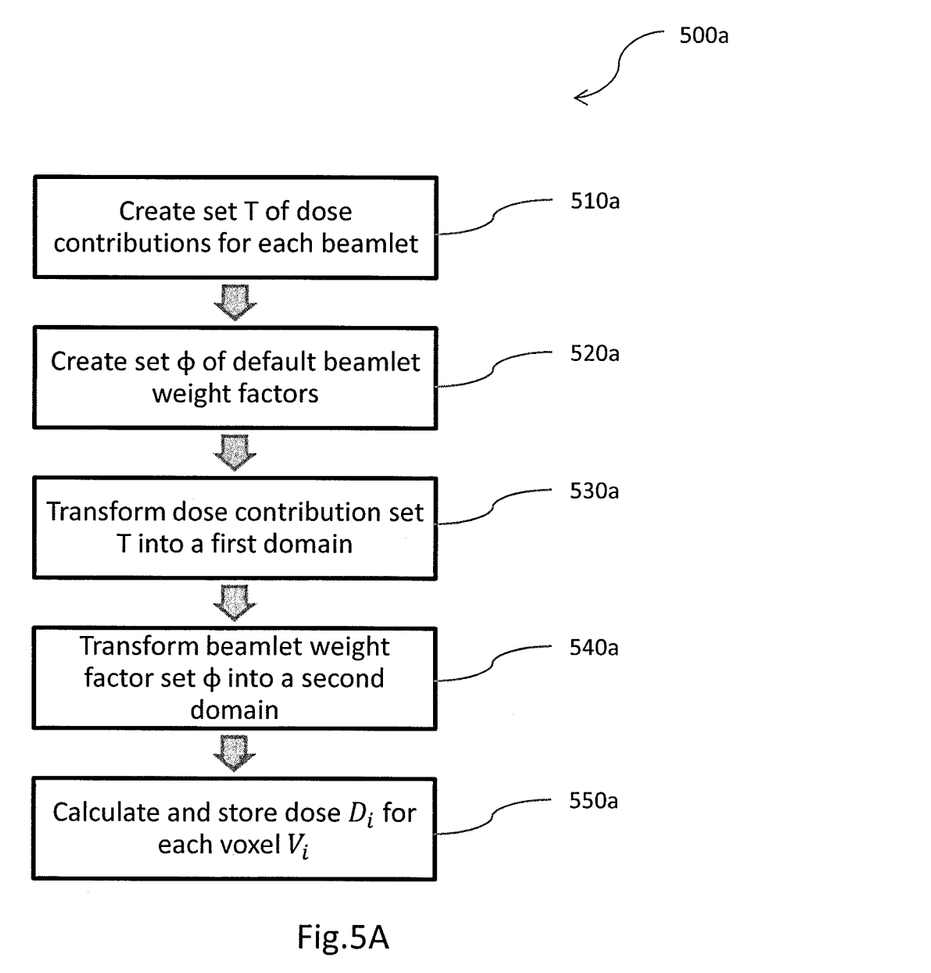
FIG. 5A is a flowchart of a dose calculation subprocess.

Referring now to FIG. 5A, dose calculation subprocess 500a is described. Dose determination subprocess 500a calculates and stores the set of dose delivered from each beamlet to each voxel in a VOI.

Subprocess 500a begins with step 510a, at which a set T of dose contribution is created. The elements of set T, so called dose contributions or elementary doses, represent the doses received by each voxel projected from each beamlet. For example, an element $T_{ij}$ of T denotes the dose contribution to a voxel i deposited by a beamlet j.

At step 520a, a set $\phi$ of beamlet weight factors is created. In some embodiments, each beamlet is set default to have equal weighting, which may be e.g. 1. In other embodiments, the weight factors may be varying for different beamlets. An element $\phi_j$ of set $\Phi$ denotes the weight factor of a beamlet j.

At step 530a, set T of dose contribution is transformed into a first domain. Said transformation of the set of dose contributions is denoted as Z. The domain Z transforms into is sparse, i.e. the information present in T is statistically concentrated in only a few coefficients of the transformed matrix Z(T).

In some embodiments, non-significant elements can be identified and dropped, in effect, rendering the matrix Z(T) sparse. The i-th row of Z(T) now contains $k_i$ significant elements, where $k_i$ is a much smaller number compared to $N_b$. This may lead to a significant reduction of the arithmetic operations of dose calculation, since $k_i \ll N_b$. In some embodiments, a single method can be applied to identify non-significant elements. In other embodiments, the method may vary across Z(T).

Further, since the majority members of Z(T) are 0, only the non-zero members of Z(T) are saved in a storage, which leads to a reduction of the storage space. Choosing the relative amount of zero-entries of Z(T) allows to adjust the trade-off between computation speed and accuracy. Or more precisely, dropping less elements of Z(T) keeps the dose D more accurate.

At step 540a, the set $\omega$ of beamlet weight factors is transformed into a second domain orthogonal to the first domain. The transformation of the set of weight factors is denoted as Y. Said transformations fullfill one basic requirement: the scalar product remains unchanged, i.e. t·$\phi$=Z(t)·Y($\phi$).

At step 550a, dose for each voxel is calculated. For example, dose $D_i$ for a voxel i can be calculated by the following expression:

$$D_i = Z(T)_{ij} \cdot Y(\phi)_j \qquad (9)$$

where the calculation runs through all the voxels in a VOI.

According to the current embodiments, dose $D_i$ is calculated by the multiplication of $Z(T)_{ij} \cdot Y(\phi)_j$, instead of $T_{ij} \cdot \phi_j$. The i-th row of Z(T) now contains $k_i$ significant elements, where $k_i$ is a much smaller number compared to $N_b$. This may lead to a significant reduction of the arithmetic operations of dose calculation, since $k_i \ll N_b$. Further, since the majority members of Z(T) are 0, only the non-zero members of Z(T) are saved in a storage, which leads to a reduction of the storage space.

Figure 5B:
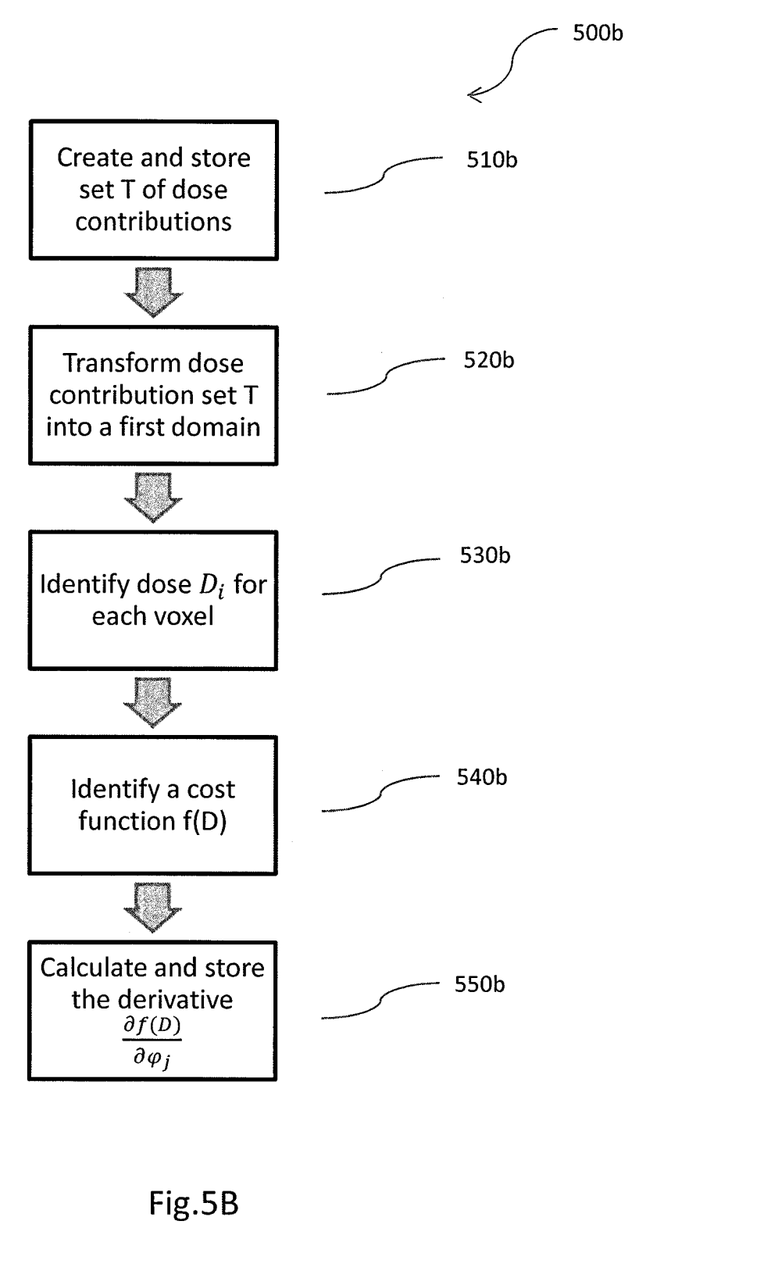
FIG. 5B is a flowchart of a cost function gradient calculation subprocess.

Referring now to FIG. 5B, the derivative calculation subprocess 500b is described. Derivative calculation subprocess 500b calculates and stores the set of derivative of a cost function with respect to each beamlet weight factor.

Subprocess 500b begins with step 510b, the same as step 510a, at which a set T of dose contributions is created. The elements of set T, so called dose contributions or elementary doses, represent the doses received by each voxel deposited by each beamlet. For example, an element $T_{ij}$ of T denotes the dose contribution to a voxel i deposited by a beamlet j.

At step 520b, set T of dose contribution is transformed into a first domain. Said transformation of the set of dose contributions is denoted as Z. The domain Z transforms into is sparse, i.e. the information present in T is statistically concentrated in only a few coefficients of the transformed matrix Z(T).

In some embodiments, non-significant elements can be identified and dropped, in effect, rendering the matrix Z(T) sparse. The i-th row of Z(T) now contains $k_i$ significant elements, where $k_i$ is a much smaller number compared to $N_b$. This may lead to a significant reduction of the arithmetic operations of dose calculation, since $k_i \ll N_b$. In some embodiments, a single method can be applied to identify non-significant elements. In other embodiments, the method may vary across Z(T).

Further, since the majority members of Z(T) are 0, only the non-zero members of Z(T) are saved in a storage, which leads to a reduction of the storage space. Choosing the relative amount of zero-entries of Z(T) allows to adjust the trade-off between computation speed and accuracy. Or more precisely, dropping less elements of Z(T) keeps the dose D=Z(T)Y($\phi$) more accurate.

At step 530b, dose for each voxel is identified.

At step 540b, a cost function of dose is defined as f(D).

The transformation in 520b needs to fullfill one basic requirement, namely that there exists an transform U such that $$x=U(Z(x))$$

for any given $N_v$-element vector x.

At step 550b, the gradient of the cost function with respect to each beamlet weight factor is calculated. For example, a gradient with respect to the weight factor of beamlet j can be calculated as:

$$\frac{\partial f(D)}{\partial \varphi_j} = \frac{\partial f(D)}{\partial D_i} T_{ij} = U\left(\frac{\partial f(D)}{\partial D_i} Z(T_{ij})\right)$$

and the calculation of this equation will run through all the beamlets.

According to the current embodiments, gradient $$\frac{\partial f(D)}{\partial \varphi_j}$$

is calculated by the multiplication and transformation $$U\left(\frac{\partial f(D)}{\partial D_i} Z(T_{ij})\right)$$

instead of $$\frac{\partial f(D)}{\partial D_i} T_{ij}.$$

Non-significant elements can be identified and dropped, in effect, rendering the matrix $Z(T)_{ij}$ sparse. The i-th row of Z(T) now contains $k_i$ significant elements, where $k_i$ is a much smaller number compared to $N_b$. This may lead to a significant reduction of the arithmetic operations of the cost function gradient calculation, since $k_i \ll N_b$.

Further, since the majority members of Z(T) are 0, only the non-zero members of Z(T) are saved in a storage, which leads to a reduction of the storage space. Choosing the relative amount of zero-entries of Z(T) allows to adjust the trade-off between computation speed and accuracy. Or more precisely, dropping less elements of Z(T) keeps the derivative of f(D) with respect to the weight factors $\phi_j$ more accurate.

Figure 5C:
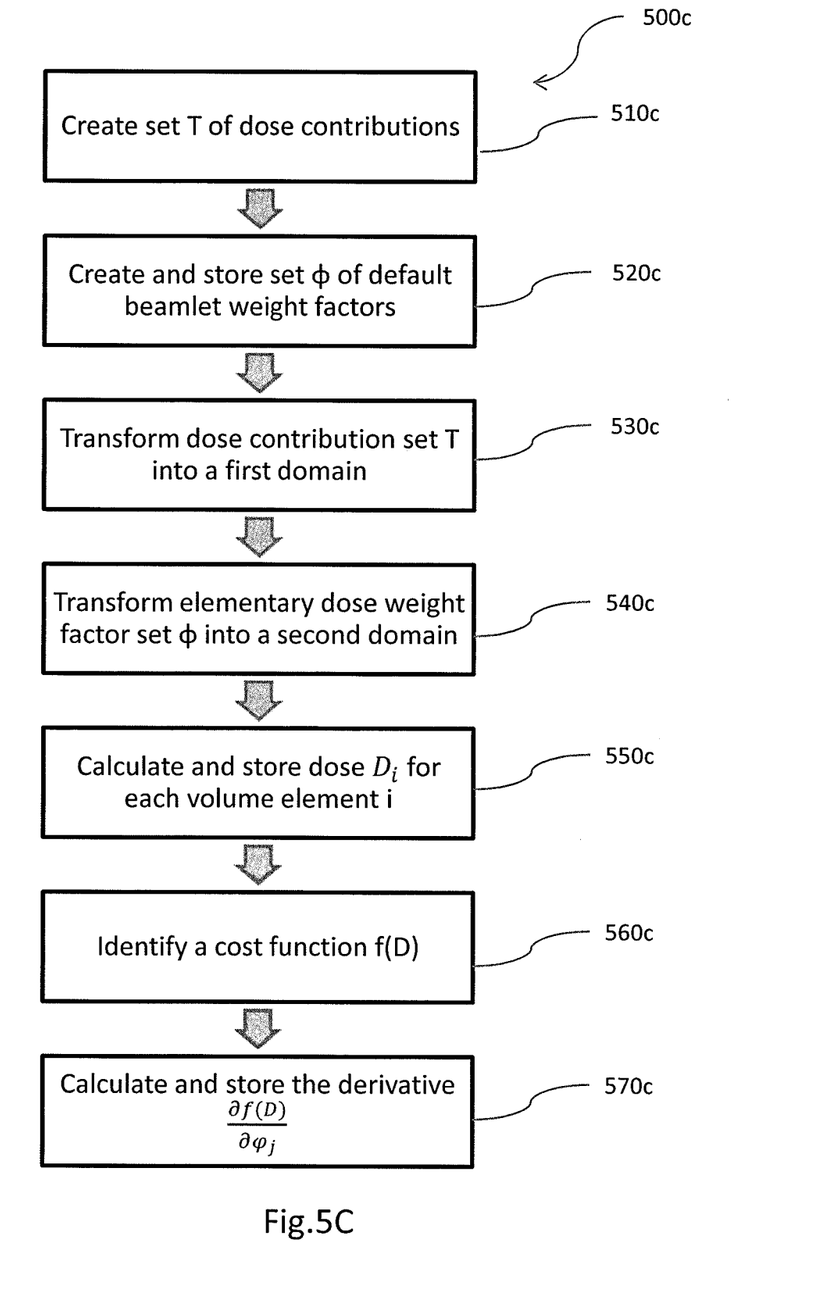
FIG. 5C is a flowchart of dose determination subprocess.

In some embodiments, the dose for each voxel and the gradient of a cost function with respect to each weight factor are calculated separately as described in subprocesses 500a and 500b. In other embodiments, aforementioned two sets of value can also be determined in a single process 500c, as will be described in detail.

Subprocess 500c begins with step 510c, the same as step 510a, at which a set T of dose contribution is created. The elements of set T, so called dose contributions or elementary doses, represent the doses received by each voxel projected from each beamlet. For example, an element $T_{ij}$ of T denotes the dose contribution to a voxel i deposited by a beamlet j.

At step 520c, the same as step 520a, a set $\phi$ of beamlet weight factors is created. In some embodiments, each beamlet is set default to have equal weighting, which may be e.g. 1. In other embodiments, the weight factors may be varying for different beamlets. An element $\phi_j$ of set $\phi$ denotes the weight factor of a beamlet j.

At step 530c, the same as step 530a, set T of dose contribution is transformed into a first domain. Said transformation of the set of dose contributions is denoted as Z. The domain Z transforms into is sparse, i.e. the information present in T is statistically concentrated in only a few coefficients of the transformed matrix Z(T).

In some embodiments, non-significant elements can be identified and dropped, in effect, rendering the matrix Z(T) sparse. The i-th row of Z(T) now contains $k_i$ significant elements, where $k_i$ is a much smaller number compared to $N_b$. This may lead to a significant reduction of the arithmetic operations of dose calculation, since $k_i \ll N_b$. In some embodiments, a single method can be applied to identify non-significant elements. In other embodiments, the method may vary across Z(T).

Further, since the majority members of Z(T) are 0, only the non-zero members of Z(T) are saved in a storage, which leads to a reduction of the storage space. Choosing the relative amount of zero-entries of Z(T) allows to adjust the trade-off between computation speed and accuracy. Or more precisely, dropping less elements of Z(T) keeps the dose D=Z(T)Y($\phi$) and the derivative of f(D) with respect to the weight factor $\phi_j$ more accurate.

At step 540c, the same as in step 540a, the set $\phi$ of beamlet weight factors is transformed into a second domain orthogonal to the first domain. The transformation of the set of weight factors is denoted as Y. Said transformations fullfill one basic requirement: the scalar product remains unchanged, i.e. t·$\phi$=Z(t)·Y($\phi$). At step 550c, the same as step 550a, dose for each voxel is calculated. For example, dose $D_i$ for a voxel i can be calculated by the following expression:

$$D_i = Z(T)_{ij} \cdot Y(\phi)_j$$

where the calculation runs through all the voxels in a VOI.

At step 560c, the same as step 540b, a cost function of dose is defined as f(D).

The transformation in 530c needs to fullfill one basic requirement, namely that there exists an transform U such that $$x=U(Z(x))$$

for any given $N_v$-element vector x.

At step 570c, the same as step 550b, the gradient of the cost function with respect to each beamlet weight factor is calculated. For example, a gradient with respect to the weight factor of beamlet j can be calculated as:

$$\frac{\partial f(D)}{\partial \varphi_j} = \frac{\partial f(D)}{\partial D_i} T_{ij} = U\left(\frac{\partial f(D)}{\partial D_i} Z(T_{ij})\right)$$

and the calculation of this equation will run through all the beamlets.

The subprocess 500 is merely depicted for a given gantry angle. However, the described method is not limited to a single gantry angle. The extension of the described method to more than one gantry angle is straightforward.

Figure 6:
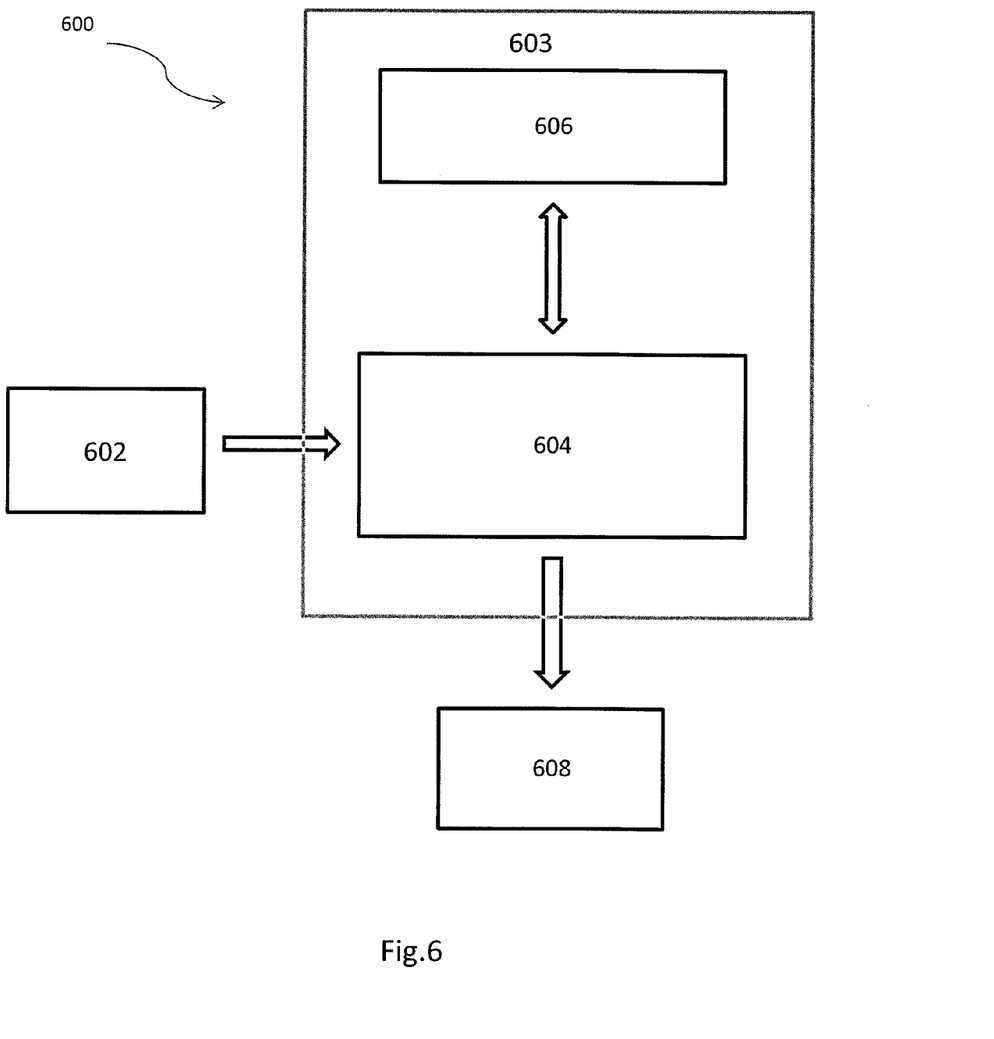
FIG. 6 is a block diagram of a system for dose determination according to described embodiments.

While the methods and subprocesses for dose determination have been described above in relation to various embodiments, the invention may be embodied also in a system 600, running dose determination module 604 and configured to perform the described methods and subprocesses, as is shown in FIG. 6.

In FIG. 6, system 600 includes a computer system 603 having memory 606 and dose determination module 604 running as executable computer program instructions thereon. The computer program instructions are executed by one or more processors (not shown) within computer system 603. Memory 606 comprises fast memory, such as fast-access RAM, for storing data sets and calculation terms used during the dose determination process 200.

Computer system 603 further includes normal computer peripherals (not shown), including graphics displays, keyboard, secondary memory, graphical processing unit (GPU), and serial and network interfaces, as would normally be used for a computer system which receives input data 602 and generates corresponding output data 608.

While embodiments of the disclosure have been described in relation to dose determination for radiation therapy treatment, it is to be understood that the dose determination process 200 and determination system 600 may be equally useful for planning dose delivery to body volumes other than those of human patient under treatment for cancerous tumors. For example, the described systems and methods may be employed for animals other than humans and may be employed for irradiation non-living tissue or material or organic matter where selective dose delivery of radiation is desired. Further, the described systems or methods can be employed for virtual models of physical objects or systems in a similar fashion.

In this description, certain terms have been used interchangeably. For example, dose contribution and elementary dose have been used interchangeably and are intended to have the same meaning. Similarly, gradient and derivative have been used interchangeably and are intended to have the same meaning. Moreover, Volume element and voxel have been used interchangeably and are intended to have the same meaning. For the sake of clarity, the Einstein notation convention is used interchangeably with the customary notation to describe summations over a range of indices.

What is claimed:

1. A method for determining a radiation dose to be administered by a radiation therapy apparatus, wherein the method comprises:

inputting a set of volume elements from a volume of interest in a physical object or system or a virtual model thereof into the radiation therapy apparatus comprising a processor, a memory, a dose determination module, and a display;

inputting a plurality of beamlets into the radiation therapy apparatus, each of said beamlets depositing a dose contribution of radiation to at least one volume element;

processing the dose contributions of all beamlets for each of said volume elements into a first domain with the processor and yielding a set of transformed dose contributions for each of said volume elements;

assigning a weight to each of said beamlets to create a set of weights;

processing the set of weights into a second domain orthogonal to the first domain with the processor and yielding a set of transformed weights;

determining a dose for each of said volume elements through summing up the elementwise products of the set of transformed dose contributions and the set of transformed weights; and displaying a visual representation of the dose for each of said volume elements on the display of the radiation therapy apparatus.

2. The method as in claim 1, wherein the first domain is sparse.

3. The method as in claim 2, wherein a scalar product of the first domain and second domain is the same.

4. The method as in claim 2, further comprising setting non-significant elements of the set of transformed dose contributions to zero; wherein said non-significant elements are identified by a threshold.

5. The method as in claim 4, further comprising assigning a threshold for each of said volume elements.

6. The method as in claim 4, wherein said non-significant elements are defined for each of said volume elements.

7. The method as in claim 1, wherein a scalar product of the first domain and second domain is the same.

8. The method as in claim 1, wherein each of said beamlets is assigned equal weight.

9. The method as in claim 1, wherein each of said beamlets is assigned with different weight values.

10. A non-transitory computer readable medium having stored thereon instructions that when executed cause one or more processors to determine a radiation dose to be administered by a radiation therapy apparatus comprising a processor, memory, and dose determination module; wherein the instructions comprise:

receiving a first input comprising a set of volume elements from a volume of interest in a physical object or system, or a virtual model thereof;

receiving a second input comprising a plurality of beamlets, each of said beamlets depositing a dose contribution of radiation to at least one volume element;

transforming processing the dose contributions of all beamlets for each of said volume elements into a first domain and yielding a set of transformed dose contributions for each of said volume elements;

storing a weight for each of said beamlets to create a set of weights;

transforming processing the set of weights into a second domain orthogonal to the first domain and yielding a set of transformed weights;

generating a dose for each of said volume elements through summing up elementwise products of the set of transformed dose contributions and the set of transformed weights; and outputting the dose for each of said volume elements to the radiation therapy apparatus.

11. A method for determining a radiation dose to be administered by a radiation therapy apparatus, wherein the method comprises:

inputting a set of volume elements from a volume of interest in a patient, into the radiation therapy apparatus comprising a processor, a memory, a dose determination module, and a display;

inputting a plurality of beamlets into the radiation therapy apparatus, each of said beamlets depositing a dose contribution of radiation to at least one volume element;

processing the dose contributions of all beamlets for each of said volume elements into a first domain with the processor and yielding a set of transformed dose contributions for each of said volume elements;

assigning a weight to each of said beamlets to create a set of weights;

processing the set of weights into a second domain orthogonal to the first domain with the processor and yielding a set of transformed weights;

determining a dose for each of said volume elements through summing up elementwise products of the set of transformed dose contributions and the set of transformed weights; and displaying a visual representation of the dose for each of said volume elements on the display of the radiation therapy apparatus.

12. A method for determining a radiation dose to be administered by a radiation therapy apparatus, wherein the method comprises performing dose:

inputting a set of volume elements from a volume of interest in a physical object or system or a virtual model thereof into the radiation therapy apparatus comprising a processor, a memory, a dose determination module, and a display;

inputting a plurality of elementary doses into the radiation therapy apparatus, each of said elementary doses depositing a dose contribution of radiation to at least one volume element of the set of volume elements;

processing the dose contributions of all elementary doses for each of said volume elements into a first domain with the processor and yielding a set of transformed dose contributions for each of said volume elements;

assigning a weight to each of said elementary doses to create a set of weights;

processing the set of weights into a second domain orthogonal to the first domain with the processor and yielding a set of transformed weights;

determining a dose for each of said volume elements through summing up elementwise products of the set of transformed dose contributions and the set of transformed weights; and displaying a visual representation of the dose for each of said volume elements on the display of the radiation therapy apparatus.

* * * * *